United States Patent [19]
Granucci

[11] Patent Number: 5,856,180
[45] Date of Patent: Jan. 5, 1999

[54] IMMORTALIZATION OF DENDRITIC CELLS WITH V-MYC ONCOGENE

[75] Inventor: Francesca Granucci, Milan, Italy

[73] Assignee: BIOTOP s.a.s. di Rita Cassarin, Milan, Italy

[21] Appl. No.: 549,666

[22] PCT Filed: May 26, 1994

[86] PCT No.: PCT/EP94/01720

§ 371 Date: Nov. 29, 1995

§ 102(e) Date: Nov. 29, 1995

[87] PCT Pub. No.: WO94/28113

PCT Pub. Date: Dec. 8, 1994

[30] Foreign Application Priority Data

May 31, 1993 [IT] Italy .................................. MI93A1118

[51] Int. Cl.⁶ .............................. C12N 5/00; C12N 15/00
[52] U.S. Cl. ........................... 435/325; 435/320.1; 435/6; 435/172.3; 435/354; 435/366
[58] Field of Search ............................... 435/320.1, 240.2, 435/6, 7.2, 240.21, 354; 935/62, 52, 55, 57, 66, 70, 71, 65; 536/23.4, 23.5; 424/93.1, 93.2, 93.21

[56] References Cited

PUBLICATIONS

Coghlan, A. New Scientist, vol. 145: 14–15, Nov. 25, 1995.
Brown, D. The Washington Post, A22, Dec. 8, 1995.
Komatsubara, et al. Microbiology and Immunology, vol. 32(8): 869–875, Aug. 1988.
Komatsubara, et al. Mem. Fac. Sci. Kyoto Univ., Series of Biology, vol. 13(1): 31–39, Jul. 1988.
Breel, et al. Imunobiology, vol. 178(3): 167–176, Mar. 1988.
Pirami et al. Proc. Natl. Acad. Sci., vol. 88: 7543–7547, Sep. 1991.
Lutz, et al. J. of Immunological Methods, vol. 174 (1–2): 269–279, Jan. 1994.
Paglia, et al. J. of Exp. Med., vol. 178 (6): 1893–1901, Dec. 1993.

*Primary Examiner*—Jasemine C. Chambers
*Assistant Examiner*—Karen M. Hauda
*Attorney, Agent, or Firm*—Oblon, Spivak, McClelland, Maier & Neustadt, P.C.

[57] ABSTRACT

The present invention refers to immortalized dendritic cells, to a process for their production from primary cultures and to their use for the activation, in vivo or in vitro, of T lymphocytes in antigen specific way.

12 Claims, 8 Drawing Sheets

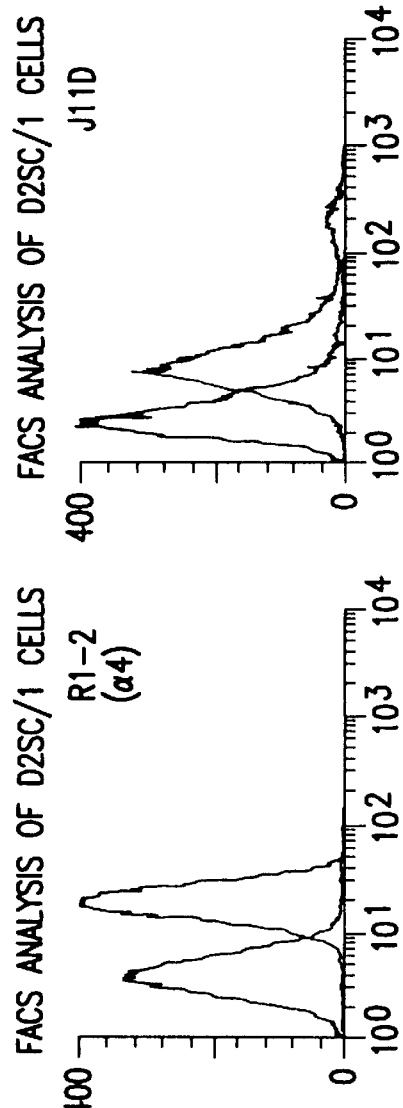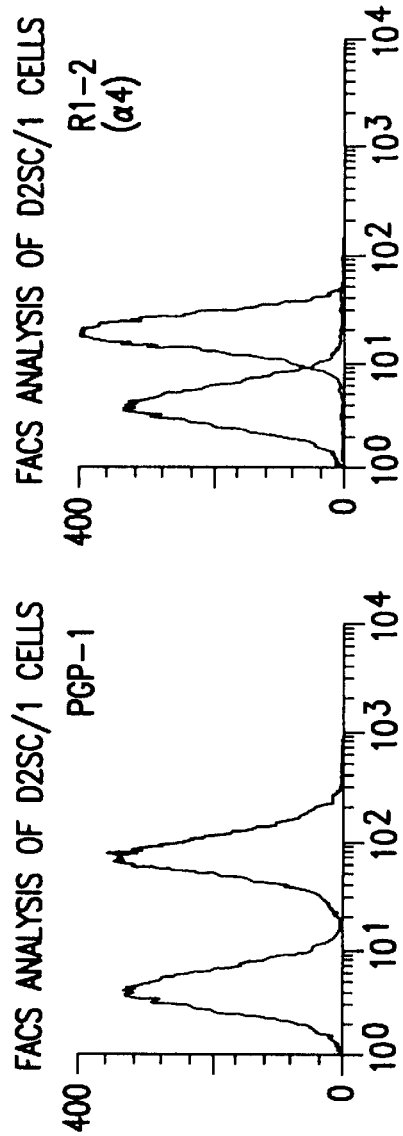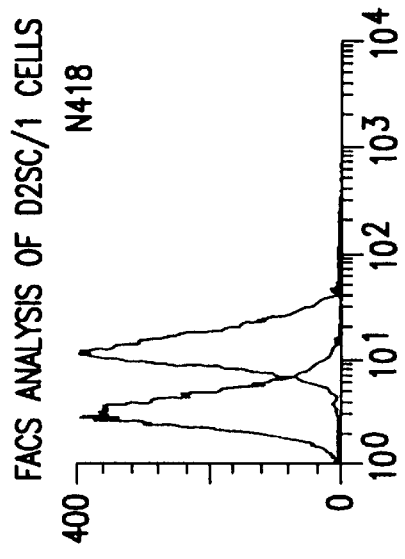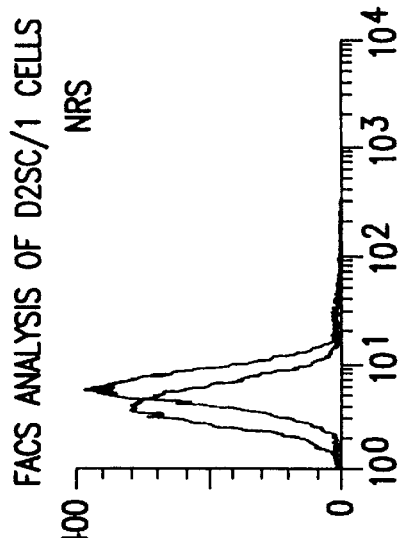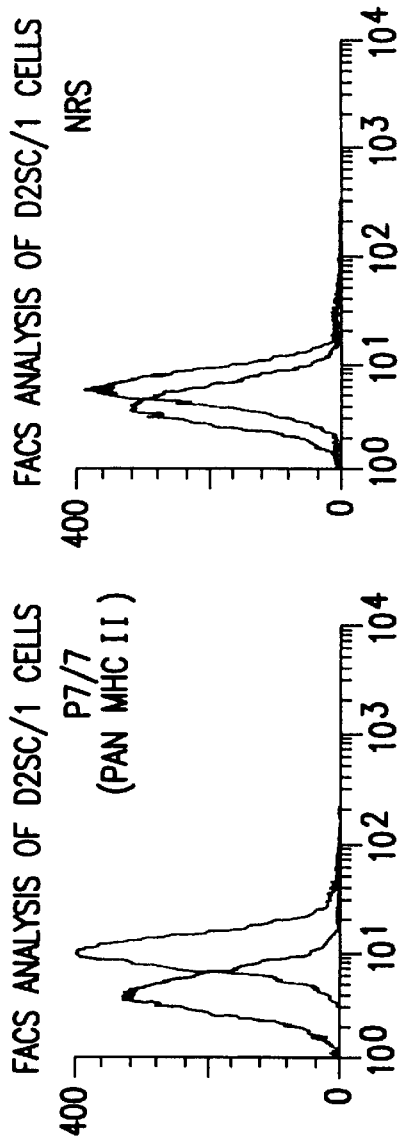

IMMORTALIZATION OF DENDRITIC CELLS WITH V-MYC ONCOGENE

This application is a 371 of PCT/EP94/01720, filed May 26, 1994.

The present invention refers to immortalized dendritic cells, to a process for their production from primary cultures and to their use for the activation, in vivo or in an vitro, of T lymphocytes in antigen specific way.

The antigen specific immune response is the result of interactions between T, B lymphocytes and antigen presenting cells (APCs). The type of immune response elicited by the antigen (cell-mediated cytotoxic or humoral responses) and the generation of immune memory are influenced by the interaction between these cells and their products, by the site where these interactions occur and by the nature of the antigen itself. It is believed that activation and suppression of the immune system are also the results of the above mentioned variables which, if not regulated, can lead to autoimmune diseases and tolerance induction.

Dendritic cells (DC), first described by Steinman and Cohn in 1973 (J. Exp. Med. 137:1142, 1973), are a population of widely distributed leukocytes that play a key role in the immune system (Steinman R. M. 1991, Annu. Rev. Immunol. 9:271–296; Romani N. et al., 1992, Spinger Semin. Immunopathol. 13:265) given that they are: i. highly specialized in antigen presentation, ii. the principal activators of resting T cells in vitro (Inaba M. D. et al., 1984, J. Exp. Med. 160:858; Croft M. et al., 1992, J. Exp. Med. 176:1431), iii. the major source of immunogenic epitopes for specific T cell clones following administration of antigen in vivo (Inaba K. et al., 1990, J. Exp. Med. 172:631; Crowley M. et al., 1990, J. Exp. Med. 172:383) and iiii. the most potent initiators of primary T cell-mediated responses in vivo (Lechler R. I. et al., 1982, J. Exp. Med. 155:31).

Several studies have suggested that DC provide naive T cells with all the necessary signals required for activation and proliferation (Steinman R. M. and Romani N., above cited). These signals are generated by the interaction of complexes of major histocompatibility complex (MHC) molecules and antigenic peptides with the T cell receptor (Davis M. et al., 1988, Nature 334:395), and by the engagement of co-stimulatory molecules, including binding of B7/BB1 molecules on antigen presenting cells (APC) to CD28 receptor on the T cell surface (Young J. W. et al., 1992, J. Clin. Invest. 90:229; Nabavi N. et al., 1992, Nature 360:266). The first signal alone elicits effector functions only in activated T cells and is unable to stimulate naive or resting T cells, which in the absence of co-stimulatory signals can enter a period of unresponsiveness (Inaba K. et al., 1985, Science 229:475; Mueller D. L. et al., 1989, J. Immunol. 142:2617; Tan P. et al., 1993, J. Exp. Med. 177:165). The expression of the co-stimulatory molecule B7/BB1 on DC populations has been recently reported and shown to be critical in DC-driven primary T cell responses (Larsen C. P. et al., 1992, J. Exp. Med. 176:1; Symington F. W. et al., 1993, J. Immunol. 150:1286; Liu Y. et al, 1992, Eur. J. Immunol. 22:2855).

Understanding the mechanisms underlying the potent stimulatory capacities of DC could explain how T cells are primed, and how the immune response is initiated. With this knowledge one might try to manipulate immune responses at very early stages and provide a way for inducing immunity or tolerance. However, an important limitation in the study of DC biology has been the small numbers of cells available from any tissue, given that no stable cell lines that are clearly similar to DC have been obtained so far.

Three different tissues have been used as major sources of DC: mouse spleen, the epidermis, where DC are known as Langerhans cells, and human blood. In each case DC constitute a tiny fraction of the starting tissue, representing about 1% of crude spleen (Steinman R. M. et al., 1979, J. Exp. Med. 149:1) or epidermal (Schuler G. et al., 1985, J. Exp. Med. 161:526; Romani N. et al., 1989, J. Invest. Dermatol. 93:600) cell suspensions and 0.1–1% of peripheral blood mononuclear cells (Freudenthal P. S. et al., 1990, Proc. Natl. Acad. Sci. USA 87:7698). More recently, Inaba and co-workers have described a method for generating DC from both peripheral blood and bone marrow precursors, but cell proliferation ceases within 1–3 weeks (1992. J. Exp. Med. 175:1157).

A different approach is to generate cell lines of DC from primary cultures and identify a method which will allow the immortalization of DC. At the present time, however, there is a need for an effective method of introducing genetic material into DC to enable them to express genetic material which they do not usually express.

Unsuccessfull attempts in this respect have been carried out by Komatsubare et al. (Microbiol. Immunol. 32(8), 869–875, 1988) who inserted V-SRC and Ha-RAS oncogenes in murine dendritic cells: immortalized dendritic cells did not show however characteristics of dendritic cells.

DISCLOSURE OF THE INVENTION

It has now been found a method to obtain cell lines with the phenotypic and functional characteristics of leukocytes able to present antigenic peptides to cells of the immune system and induce specific immune responses in vivo and in vitro. In particular, the invention concerns the immortalization of antigen presenting cells (APC) such as the dendritic cells (DC) by introduction of exogenous genetic material, not expressed normally by these cells, able to generate indefinite cell growth (immortalization) in the transfected or infected cells without affecting their APC function.

The immortalized APC according to the invention have inserted and express the exogenous genetic material.

The genetic material able to immortalize APC and in particular DC, is either:

1) RNA or DNA which can be normally present in APC but not expressed to levels which could be of biological significance;
2) RNA or DNA normally present in APC but not expressed to levels which could be of biological significance, modified in order to be expressed in APC and in particular in DC;
3) RNA or DNA not normally present in APC and in particular in DC or combinations therefrom useful for their expression in APC and in particular in DC.

The genetic material able to immortalize APC and in particular DC can be:

a virus or a retrovirus or a complex of viruses or retroviruses or part of them obtained from any kind of species;

any RNA or DNA or combinations of them obtained from viruses or retroviruses or from their recombination;

any modified (either spontaneously or engineered) RNA or DNA of viral or retroviral origin or their combination.

The genetic material (any RNA, DNA or combinations or modifications of them) can be inserted in:

vectors;

expression vectors;

DNA different from the original viral or retroviral genomes;

vectors containing genetic markers for selection of the cells in which the genetic material has been inserted.

In general, the specific order in which the different elements are assembled together is not critical, so that the flanking regions might be first bound to a replication system including a marker or other regions, such as enhancers, transcriptional regulatory regions, or the like, prior to insertion of the gene. The process in which the various fragments are brought together will depend on a number or factors related to ease of construction, choice of restriction sites, use of selection methods, availability of particular fragments, and the like, which ultimately are within the choice capability of the man skilled in the art.

The genetic material allows the immortalization of APC directly from primary cultures in which DC may represent a minor population, without any need of particular selection methods.

In particular, the exogenous genetic material allowing the achievement of the above cited results derive from retroviral vectors containing the v-myc oncogene. Preferably, the retroviral vector is obtained by co-transfection of two retroviruses, at least one of them containing the v-myc oncogene.

According to a specific embodiment of the invention, the exogenous genetic material contains a retroviral oncogene of avian origin fused with a coding retroviral sequence of mouse origin; in particular, the avian oncogene is a mutated v-myc gene fused with part of the env protein derived from avian retrovirus $MH_2$ (T. Graf et al., Biochim. Biophys. Acta, 516, 269–299, 1982) and from the murine AKR retrovirus (R. Risser et al., Ann. Rev. Genet., 17, 85–121, 1983) and in "RNA Tumor Viruses", R. Weiss et al., 2nd ed. Cold Spring Harbor, 1985. More particularly, as shown in FIG. 1a, the $MH_2$ and AKR retroviruses are co-transfected into murine macrophages as disclosed by Righi et al., Oncogene, 4, 223–230, 1989. A cell line is obtained which produces a retrovirus complex (3RV) which can immortalize cells of the same type (Righi et al., Eur. J. Immunol. 19, 1443–1448).

By infecting brain macrophages with this retrovirus complex, the cell line N11 is obtained, which in turn produces the virus VN11 (Righi et al., Oncogene, 6, 103–111, 1991) which is able to immortalize macrophages (L. Pirami et al., Proc. Natl. Acad. Sci. USA 88, 7543–7547, 1991). The N11 cell line was deposited according to the Budapest Treaty at the European Collection of Animal Cell Cultures, Salisbury, UK, on Dec. 5, 1993, under the accession number 93051207.

The VN11 virus may be used to directly immortalize dendritic cells or it may be cloned into a vector able to transfect "packaging" cell lines producing retroviral vectors which are in turn able to transfect dendritic cells.

The transfection of the latter may be obtained by co-cultivating dendritic cells with "packaging" cells. Examples of "packaging" cell lines which may be used according to this invention are the psi2 cell line, disclosed in "Experimental Manipulation of gene expression" M. Inouy (ed.), 155–173, 1983 and in R. Hann et al. Cell, 33, 153–159, 1983; an equivalent derivative of psi2 cell line, named psi am, is disclosed by R. Clone et al., Proc, Natl. Acad. Sci. USA, 81, 0349–6353 and deposited at the American Type Culture Collection (Rockville, Md.-USA; accession number CRL 8859).

The genetic material preferably used for transfection, according to the invention, contains the mutated v-mycMH2 gene fused with part of the envAKR mouse retroviral sequence (EMBL Database entry Accession n. Z 26309).

The described method of immortalization of APC which uses this particular recombinant oncogene can be extended to any other cellular or retroviral oncogenes.

Because genes can be introduced into DC using a retroviral vector, they can be "on" (subject to) the retroviral vector control; in such a case, the gene of interest is transcribed from a retroviral promoter. A promoter is described as a specific nucleotide sequence recognized by a number of transcription factors in order to allow RNA polymerase complexes to initiate the RNA synthesis. Retroviral vectors can be designed in order to have other promoter elements (in addition to the promoter of the recombinant retrovirus) which are responsible for the transcription of the gene. For example, it is possible to modify the vector inserting an additional promoter modulated by external factors allowing to control the level of polypeptide being produced by the DC by adding to the culture that external factors.

Incorporation of this promoter or another promoter influenced by external cues also makes it possible to regulate the production of the polypeptide by the engineered DC.

The cell lines obtained with the introduction of the exogenous genetic material and which are part of the invention, have in addition to other properties, the characteristics of APC and the capacity to activate cells of the immune system such as T lymphocytes.

Preferred APC are DC. According to the above description, the exogenous genetic material has been introduced in DC; for the purposes of the invention DC comprise DC from bone marrow, peripheral blood, cord blood, epidermis (Langerhans cells), follicular and interstitial DC from germinal centers and interdigitating DC of the lymphoid organs. The tissue origin is not a limitation for the present invention.

The genetic material introduced in these cells confers to DC immortalization (unlimited cell growth) and can be modified in such a way that the product is changed and/or its expression can be either constitutive or inducible after activation. The product of such genetic material can be any polypeptide, secreted or anchored in the cell membrane, such as an antigen or related peptide, a lymphokine or membrane protein.

In addition, the genetic material described above can also be introduced in other cell types able to activate the immune system, such as, for instance, macrophages or into cells normally unable to activate the immune system which have been modified or induced to obtain such effect.

The invention also refers to a method to induce the immune system of an organism to generate a specific, predetermined immune response using the cell lines which are the object of the invention.

The cell lines which are the object of the invention can be loaded in vitro with any kind of antigen and then be used with the following advantages:

1) they can activate T lymphocytes ex vivo. Co-culture of naive or antigen-specific T lymphocytes with the antigen-loaded DC cell line (as antigen presenting cells) can result in priming and expansion of the antigen-specific T lymphocytes. This will be of particular interest for those antigens which either do not generate in vivo a protective immune response (for instance tumor antigens or pathogens such as viruses, fungi and intracellular parasites) or could not be used in vivo for their undesirable side effects. Antigen-specific T lymphocytes activated and expanded in vitro using DC cell lines, can be reintroduced in the organism of origin (adoptive transfer) and generate the desired immune response.

2) They can be used directly in vivo to activate the desired host antigen-specific T lymphocytes. This type of cell vaccination could be extremely useful when the introduction of the antigen into the organism is not desirable or when the pathogen is already present into the organism or when the processed antigen (peptide-MHC complex) is more suitable for vaccination compared to the whole soluble pathogen.

3) They can generate immunological memory since they can prime virgin T cells as well as induce memory T cells in vivo; this is particularly relevant in cell vaccination. In this regard, they can be considered as natural adjuvants.

4) They can be loaded with antigens which could be associated with either class I or class II MHC molecules depending on the type of immune response desired. In fact, genes coding for antigenic determinants of pathogens such as viruses or intracellular bacteria can be transfected into DC cell lines and their products will be primarily associated with class I MHC molecules; conversely DC cell lines could also be loaded with purified or recombinant proteins from pathogens such as viruses or intracellular bacteria and primarily associated with class II MHC molecules; in this way it is possible, depending on the type of loading of DC cell lines, to direct in vivo the immune response (cell-mediated or antibody mediated) by injecting either type of pre-loaded DC cell line.

5) They can be used to induce antigen specific immune responses toward antigens that depend on non MHC class I or class II antigens, such as in the case of the CD1 family.

6) They can be used to induce specific T Helper cell subsets, such as the TH1 or TH2 subsets, in those cases in which the immune system is not able to develope the desired response.

7) They can be modified with genes which can express products able to modulate the immune response, such as cytokine genes. These genes can be under the control of promoter/enhancer elements which may be induced through specific signaling pathways following the interaction between membrane receptors and ligands.

8) They can be modified in order to render them not viable when introduced in human beings by rendering them, as an example, depending on a factor or a culture condition or a molecule that is not normally present in mammals.

A) CB1 cells;

B) positive control.

Viral transcripts of genomic and subgenomic size are show by the arrows.

FIG. 2:

a)–f) FACS analysis D2SC/1 dendritic cell clones using a panel of antibodies and compared with frends dendritic cells as reported in the literature.

g)–i) Immunohistochemical analysis of CB1 cells using 2A1 (A) and M342(a) antibodies and compared with the relative controls, respectively (B) and (D).

Figure 1A:
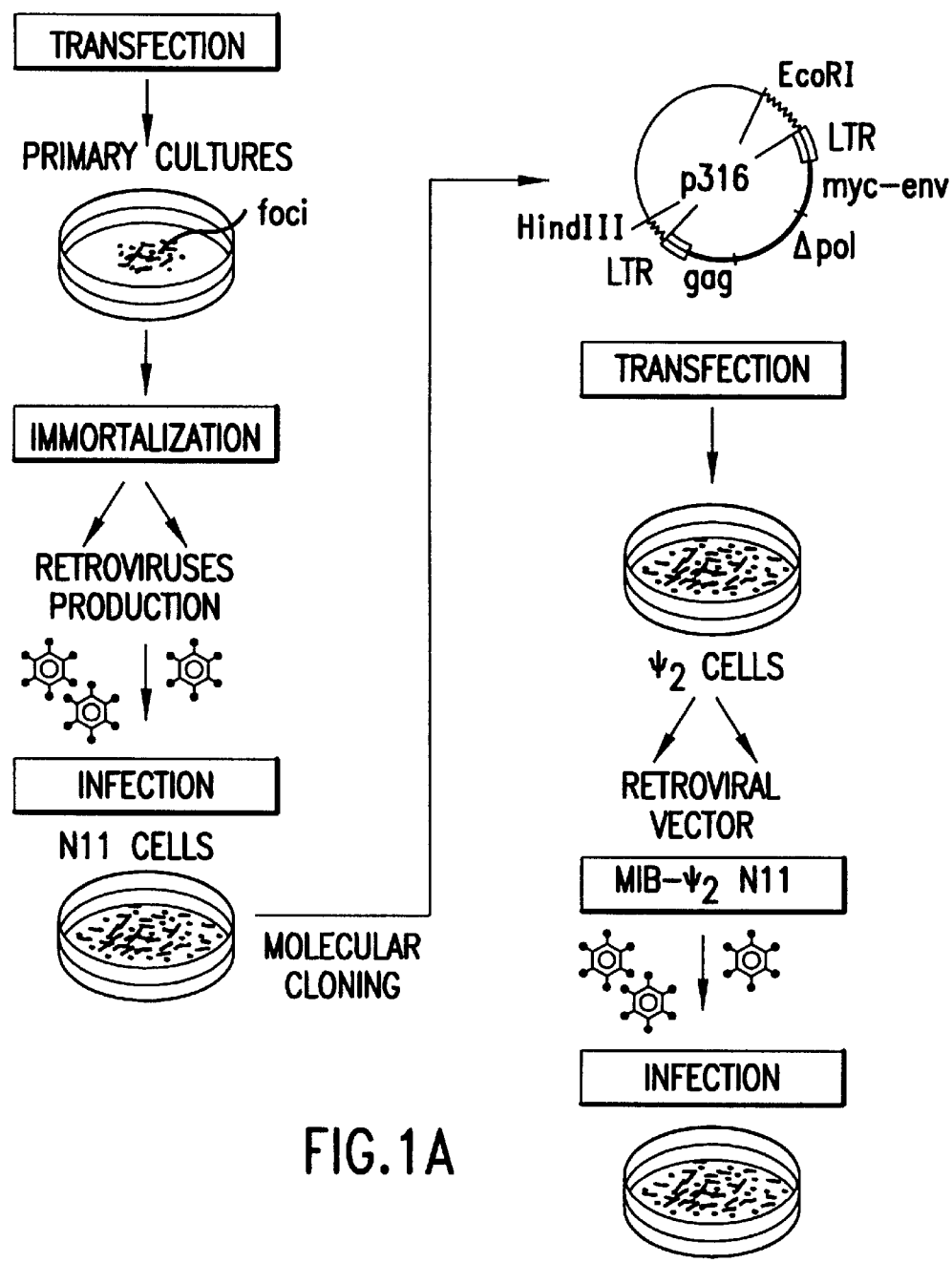
FIG. 1a: preparation scheme of the retroviral vector MIB-psi2-N11.
Figure 1B:
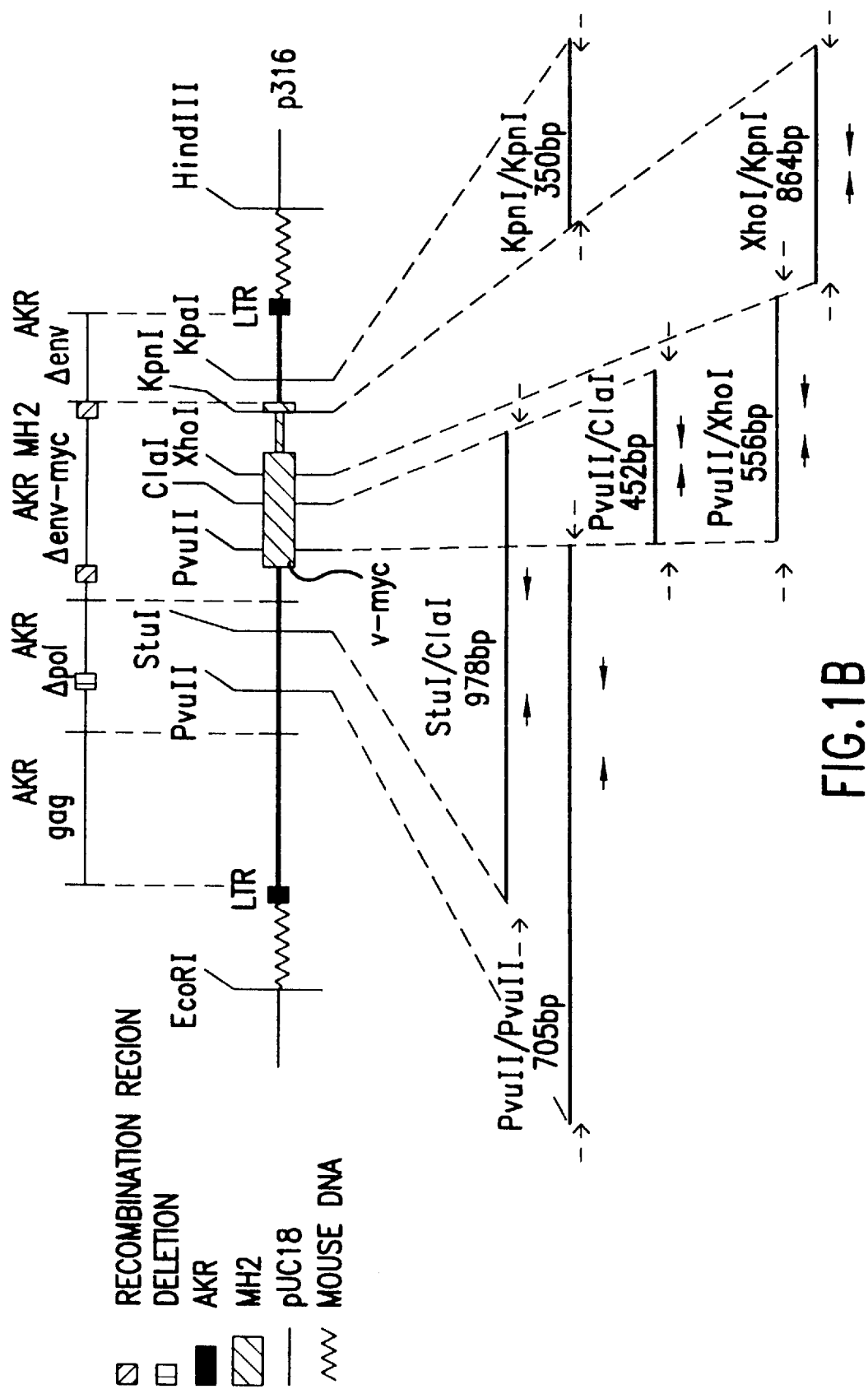
FIG. 1b: partial restriction map of the retroviral vector MIB-psi-N11.
Figure 1C:
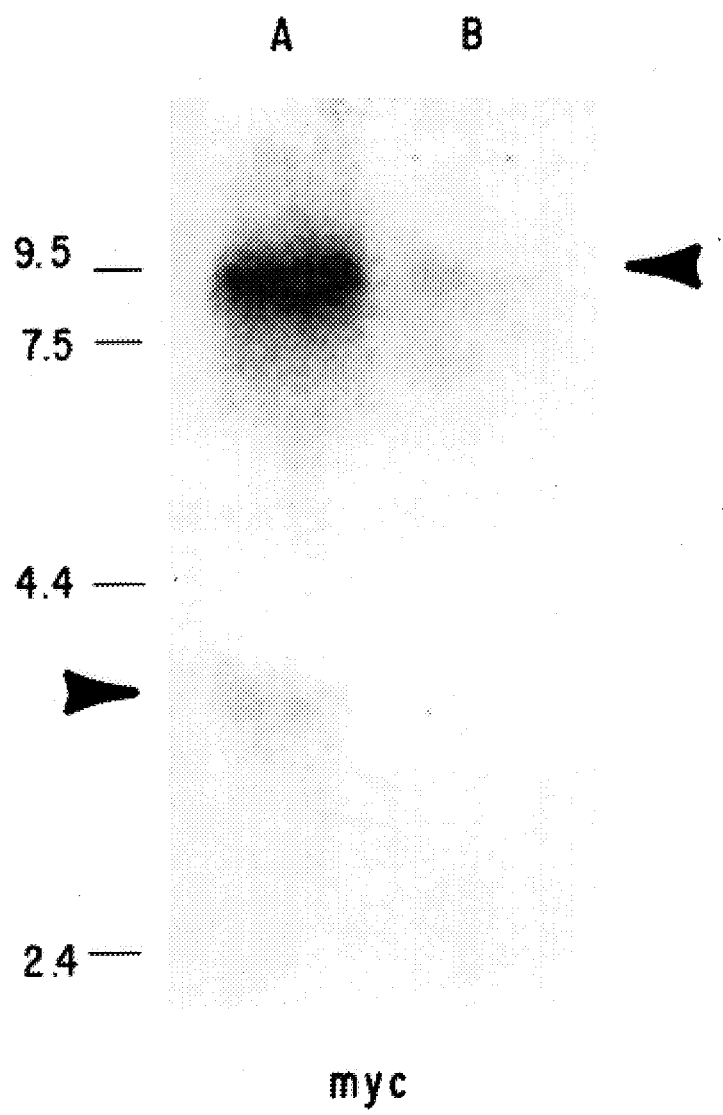
FIG. 1c: and Northern blot analysis of CB1 cell line of the invention using a specific probe for the avian gene v-myc-MH2.
Figure 2G:
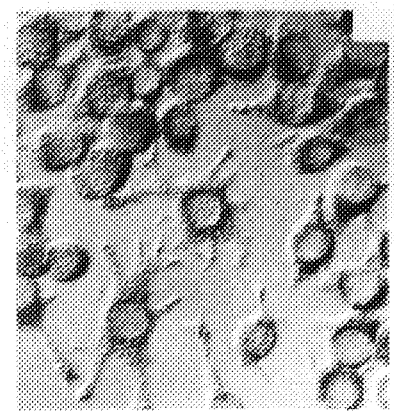
Figure 2H:
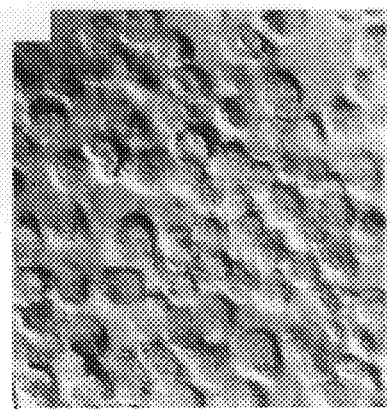
Figure 2I:
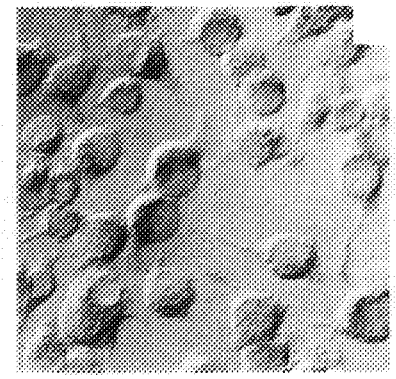
Figure 2J:
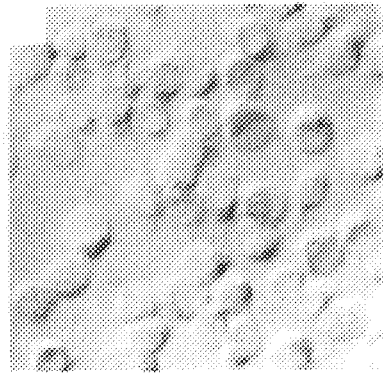
Figure 3:
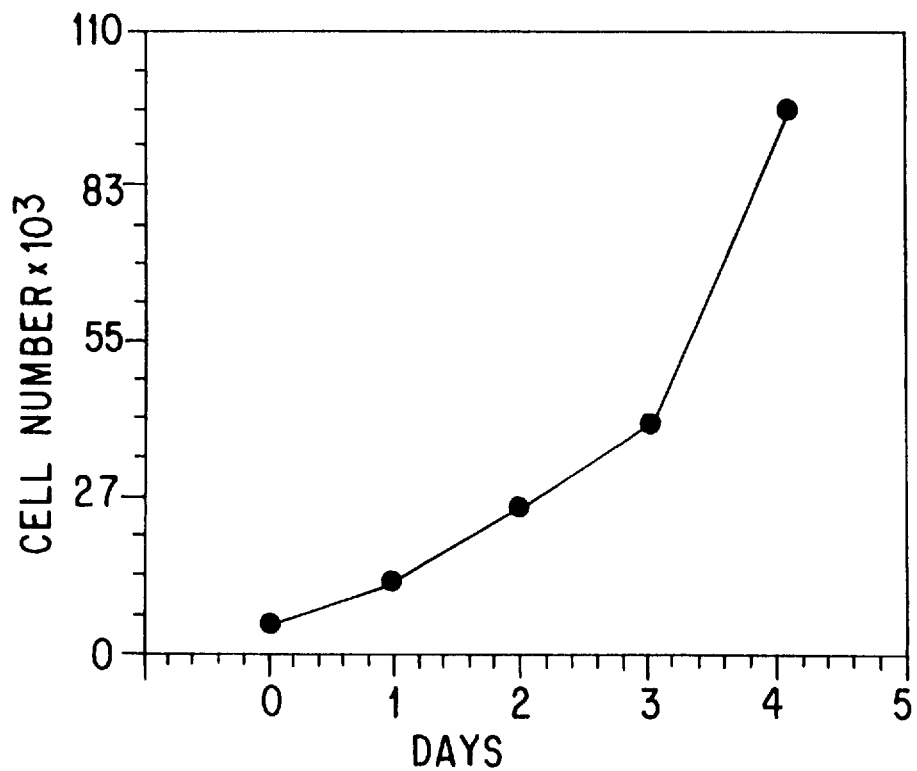
Figure 4A:
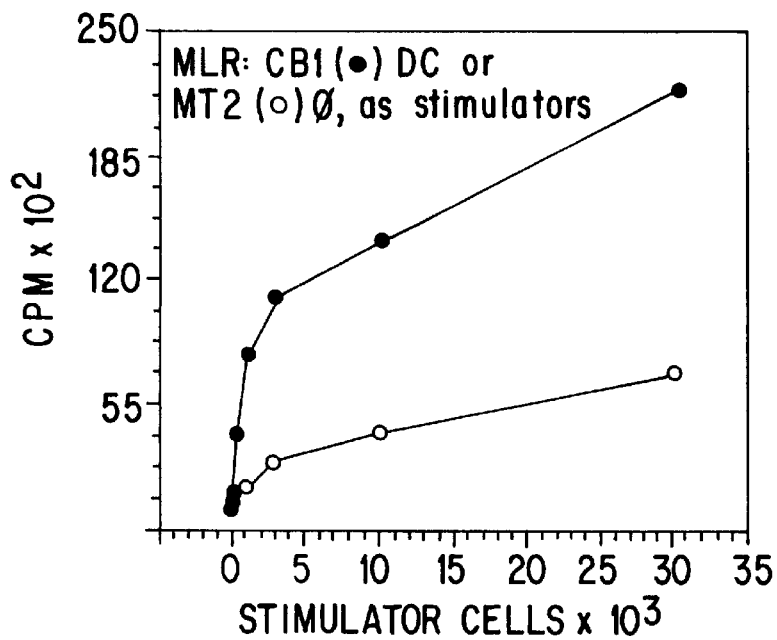
Figure 4B:
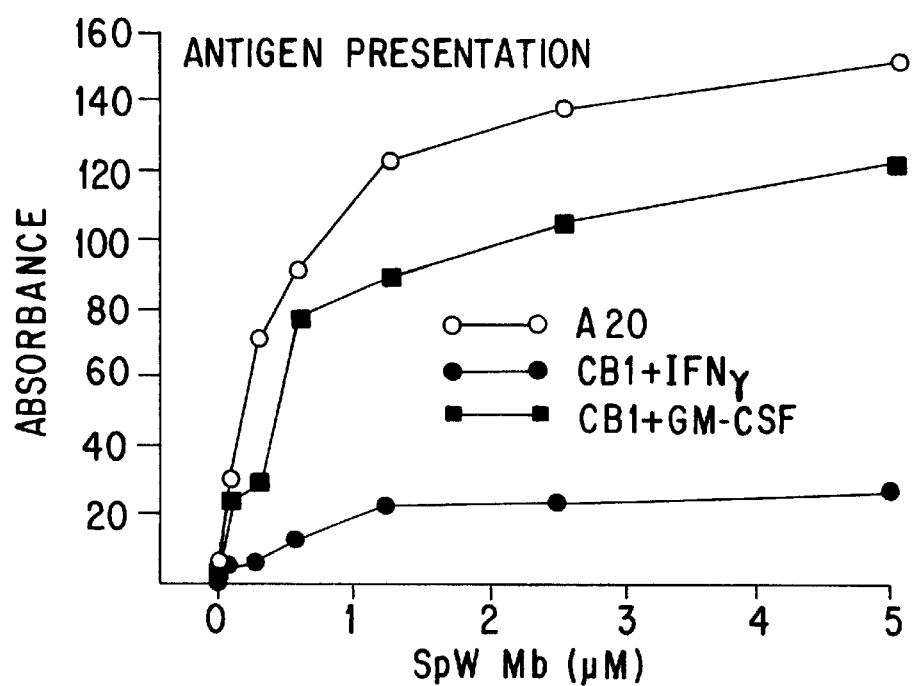

FIG. 3: Growth curve of an immortalized DC clone.

FIG. 4:

a) MLR assay;

b) antigen specific T-lymphocyte activation assay.

Figure 5A:
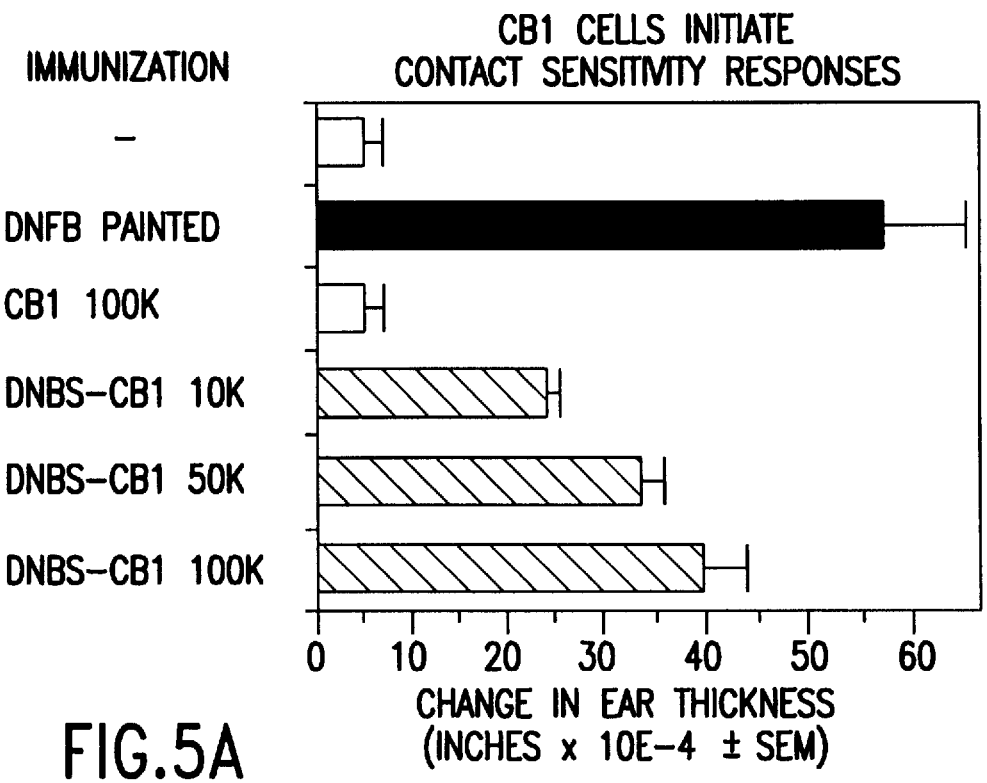
Figure 5B:
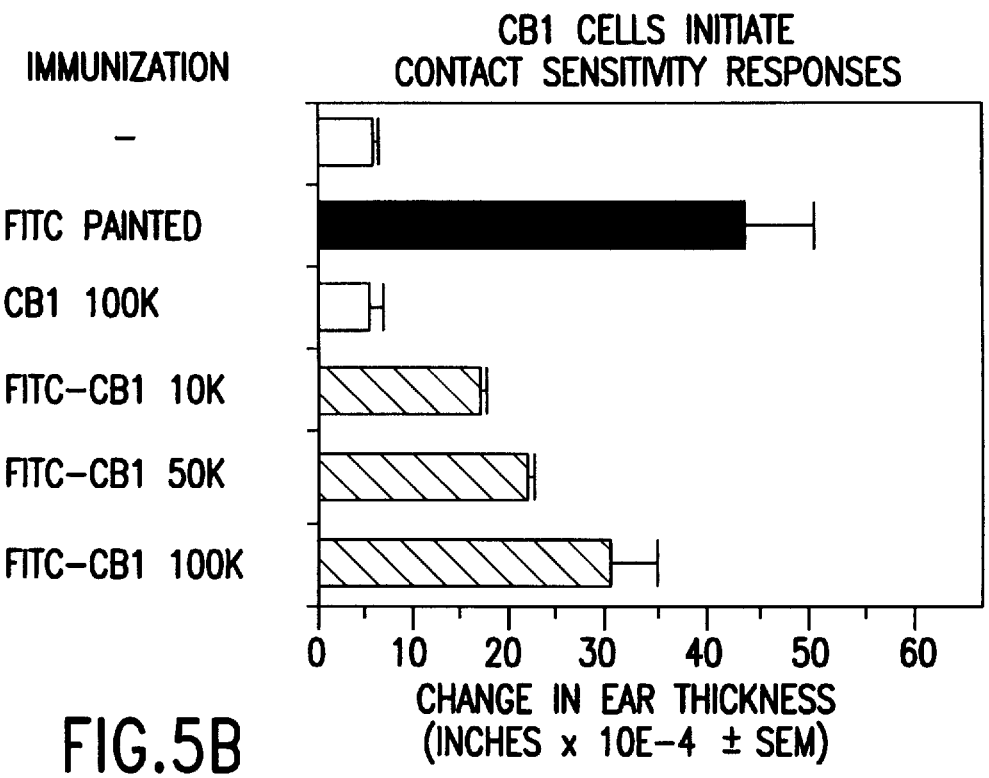

FIG. 5: Contact sensitivity (CS) induction by CB1 cells modified with FITC(a) or DNBS(b).

DETAILED DESCRIPTION OF THE INVENTION

From primary tissue cultures in which APC represent only a minor fraction of the starting material, it is possible to transduce into APC and in particular into DCs (for the purposes of the invention, DCs comprise DC from bone marrow, peripheral blood, cord blood, epidermis (Langerhans cells), follicular and interstitial DC from germinal centers and interdigitating DC of the lymphoid organs) exogenous genetic material able to generate continuous cell lines of functional APC and in particular of functional DCs. Primary cultures can be obtained from spleen cell suspensions. The cultures are typically heterogeneous mixtures of many cell types, each of which can be induced to replicate a limited number of generations. Primary cells are thus distinguishable from cell lines, which have been immortalized as a result of an ancestral transformation event or other mutation resulting in continuous or indefinite growth in culture. After about three weeks and without any kind of selection it is possible to isolate proliferating cells and establish continuous cell lines which can be further cloned.

The immortalization is achieved with genetic material consisting of an RNA or DNA construct which, in order to provide transforming capability, incorporates at least one oncogene, which can be derived from viral or cellular genomes or mammalian or avian chromosomal DNA. In general, infection of an appropriate target cell with an acutely oncogenic retrovirus leads to oncogenic transformation. Although the mechanisms leading to oncogenesis are not clearly understood, numerous viral oncogenes or v-oncs, as well as their cellular homologues, known as proto-oncogenes or c-oncs, have been catalogued. Several mechanisms have been proposed by which c-oncs acquire transforming capabilities, including control by strong viral promoters, gene copy amplification, addition of viral enhancer sequences, rearrangement, and mutation. For purposes of the present invention oncogenes include any genomic material or materials substantially homologous to oncogenic sequences which are capable of transforming a primary APC. As example of potential transforming genomic materials lists of oncogenes are provided by Bishop et al., in Weiss et al., eds., RNA Tumor Viruses, Volume 1 (Cold Spring Harbor Laboratory, NY 1984) pp 1004–1005, and Watson et al., Molecular Biology of the Gene, 4th Ed., Vol. II, (Benjamin Cummings, Menlo Park, Calif.) pp 1037. Included are the known oncogenes such as src, yes, abl, fps, fes, erbB, fms, ros, kit, mos, raf, H-ras, K-ras, sis, myc, myb, fos, ski, and erbA. Several oncogene products appear to be homologues of growth factors, growth factor receptors, or are nuclear proteins whose effects can be mimicked by the addition of their products to the cell culture. Many oncogenes can be obtained from public collections of deposited biological materials.

A combination of various retroviruses, including hybrid retroviruses generated by spontaneous recombination in vitro or retroviruses in which genes have been fused and fusion products generated, can also be used for the immortalization of cells. These events can be obtained by infection of myeloid cells with retroviruses according to the described procedures (Righi et al., 1989, Oncogene: 4, 233–230; Blasi E. et al., Nature: 318, 667–669 (1985)) and according the mechanisms described in: Weiss et al. eds. RNA tumor viruses, Cold Spring Harbor Laboratory, 1985.

A limitation of these procedures is represented by the fact that the transduced genetic material is not characterized and once introduced into the target cell could generate a viral progeny. These are undesired features particularly when the obtained cell lines have to be injected into an organism.

This invention can overcome these problems: in particular, one of the provirus able to immortalize DC cells in vitro has been molecularly cloned in a lambda phage. The insert, containing the whole viral genome plus the flanking regions derived from the mouse cell from which the provirus was originally cloned, was then subcloned in a pUC18. Useful plasmid vectors for amplifying the retroviral genetic elements in bacterial hosts prior to transfection are constructed by inserting a retroviral DNA sequence encoding the elements described previously in a vector that could include one or more phenotypic selectable markers and an origin of replication for bacterial hosts, such as *E. coli.*, although others may also be employed as a matter of choice. Thus, a useful mammalian/bacterial shuttle vector can comprise a selectable marker and bacterial origin of replication derived from commercially available plasmids comprising genetic elements of the well known cloning vector pBR322 (ATCC 37017). The resulting recombinant retrovirus would thus be capable of integration into the chromosomal DNA of an infected host cell, but once integrated, be incapable of replication to provide infective virus, unless the cell in which it is introduced contains another proviral insert encoding functionally active trans-acting viral proteins. The plasmid p316 was transfected into psi cells (packaging cell line) [Mann et al., Cell. 33:153 (1983)] which confer a limited ecotropism. The transfection can be carried out by any convenient means such as micro injection, DEAE-dextran mediated transfection, calcium phosphate precipitated DNA transfection and electroporation (see Bonerji, J. et al., Cell 33, 729–740 (1983); Graham F. L. and Van der Eb A. J., Virology, 52, 456–467 (1983) and Potter H. et al., Proc. Natl. Acad. Sci. USA, 81, 7161–7165 (1984)). The viral particles produced by the transfected packaging cell line can infect DC with a limited tropism inducing their in vitro proliferation and allowing the isolation of cell lines from these cell derivatives.

The infected DC are immortalized by these defective retroviruses but will not propagate them any further. Retroviruses to be adapted for use in accordance with this invention can be derived from many avian or mammalian hosts. However, a requirement for use is that the virus be capable of infecting cells which are to be the recipients of the new genetic material to be transduced using the retroviral vectors. Examples of retroviruses include avian retroviruses such as avian erythroblastosis virus (AMV), avian leukosis virus (ALV), avian myeloblastosis virus (ABV), avian sarcoma virus (ASV), Fujinami sarcoma virus (FuSV), spleen necrosis virus (SNV), and Rous sarcoma virus (RSV); bovine leukemia virus (BLV); feline retroviruses such as feline leukemia virus (FeLV) or feline sarcoma virus (FeSV); murine retroviruses such as murine leukemia virus (MuLV), mouse mammary tumor virus (MMTV), and murine sarcoma virus (MSV); rat sarcoma virus (RaSV); and primate retroviruses such as human T-cell lymphotropic viruses 1 and 2 (HTLV-1,2), and simian sarcoma virus (SSV). Many other suitable retroviruses are known to those skilled in the art. A taxonomy of retroviruses is provided by Teich, in Weiss et al., eds., RNA Tumor Viruses, 2d ed., Vol. 2 (Cold Spring Harbor Laboratory, New York, 1985) pp 1–16. The limited ecotropism of the retroviruses can be overcome using the cloned viral genome which can be transfected into the target cells by electroporation, protoplast cell fusion or calcium phosphate precipitation.

For example, the cell which are the object of the present invention can be obtained by infection of unselected DC with the mutated avian oncogene v-mycMH$_2$ (Graf T., Biochim. Biophys. Acta, 516, 269–299, 1982) fused with part of the env AKR mouse retroviral sequence (Risser R. et al., Ann. Rev. Genet. 17, 85–121, 1983). This sequence is found in the macrophage-derived cell line N11, producing the VN11 virus (Righi et al., Oncogene, 6, 103–111, 1991) which is able to immortalize macrophages (Pirami L. et al., Proc. Natl. Acad. Sci. USA, 88, 7543–7547, 1991). The cell line N11 has been deposited according to the Budapest Treaty at the European Collection of Animal Cell Cultures, Salisbury, GB, on May 12, 1993 under the accession number 93051207.

The VN11 virus may be directly used to immortalize dendritic cell or it may be cloned into a vector which may be transfected into "packaging" cell lines.

Dendritic cells may then be infected by co-cultivation with said "packaging" cells, or by supernatants from these packaging cells.

For instance, a retroviral vector, named MIB-psi2 N11, was obtained transfecting into the psi cell line the genome of VN11 virus, cloned into a suitable plasmid vector, together with the neo gene, derived from the TN5 transposon.

The plasmid vector may be obtained according to conventional method, e.g. by inserting Hind III-EcoRI fragments of a DNA library of N11 cells into pUC18, transformation of HB101 *E. coli* cells with the obtained constructs and subsequent screening by hybridization with a labelled probe derived from a fragment of the myc-MH2 gene.

DC can be either infected with MIB-psi2 N11 retroviral vector or they can be co-cultivated with the viral producer psi cells (psi2-N11). As an example of the co-culture procedure, psi line producing the virus can be treated with mitomycin C at 5 micrograms per ml at about 37° for about two hours in RPMI 1640 without serum. psi cells were treated with mitomycin C on a 10 centimeter dish and washed several times with DME. The suspension of spleen cells was then seeded onto this dish and left for about 24 hours spleen cells are then recovered by gentle pipetting and replated into a different petri dish.

Retroviral Vectors

Details of the construction of a retroviral vector are contained in Mulligan R. C., Construction of Highly Transmissable Mammalian Cloning Vehicles Derived from Murine Retroviruses, In: Experimental Manipulation of Gene Expression, M. Inouye (ed), 155–173 (1983); Mann R. et al., Cell, 33: 153–159 (1983); Williams D. A. et al., Nature, 310: 476–480 (1984).

The teachings of these publications are incorporated herein by reference.

The psi2 cell line described by Mulligan and co-workers was created by transfecting NIH 3T3 fibroblasts with pMOV-psi-, which is an ecotropic Moloney murine leukemia virus (Mo-MuLV) clone. pMOV-psi- expresses all the viral gene products but a sequence necessary for encapsidation of the viral genome. Moreover, pMOV-psi expresses an ecotropic viral envelope glycoprotein which recognizes a receptor present only on mouse (and closely related rodent) cells.

Another cell line is the NIH Psi am a modified pMov-Psi-genome in which the ecotropic envelope glycoprotein has been replaced with envelope sequences derived from the amphotropic virus 4070A yelding a cell line producing a recombinant virus with wider amphotropic host range.

In addition, the plasmid containing the viral genome can be modified prior to transfection into the packaging psi cell line with exogenous genetic material from other species and then introduced into DC. The introduced genetic material can be a genetic marker or selection genes coding for intracellular, membrane bound or secreted polypeptides that would further allow the identification and selection of the immortalized DC cells. The genetic material can also contain regulatory sequences or sequences able to stabilize mRNA products, such as the 3' untranslated regions of some messenger RNAs or intron regions. The provided dominant selectable marker can be, for example, any antibiotic resistance phenotype such as neo (G418 resistance), hygro (hygromycin resistance), or gpt (mycophenolic acid resistance) genes that can be used provided that a suitable donor is selected as source of the DC to be immortalized; such selectable markers, are widely available among researchers. An additional useful genomic material to be inserted into the vector is any gene product having value or utility that depends upon the environment in which it is translated, for example viral, bacterial or tumor cell antigens, or biologically active molecules such as antigen processing polypeptides, cytokines, hormones, growth factors as well as their receptors or homologues of the foregoing or any polypeptides that has a tissue specificity.

In particular genes coding for protein antigens or peptides derived from these antigens, as well as secreted lymphokines or membrane proteins such as MHC polypeptides, can also be introduced in the original MIBpsi-2-N11 vector.

Using the MIBpsi2-N11 vector several DC clones have been immortalized and two of them named CB1 and D2SC/1 extensively characterized and reported as an example. In one embodiment of this invention, the fibroblast cell line used as the feeder layer for (in cocultivation with) DC is a Psi am line producing the VN11 virus.

Spleen cell suspensions from newborn DBA/2 (CB1 cells) or BALB/C (D2SC/1 cells) mice were infected with the retroviral vector MIBpsi2-N11 and about two to four weeks after infection, foci were observed and proliferating cells, detaching from adherent aggregates, were cloned; characteristically, these cells display sheet-like processes, with a striking motility which is not exhibited by other leukocytes. The estimated doubling time of the immortalized cell lines is about 20 hrs.

Two clones, named CB1 and D2SC/1 have been characterized more in detail also by means of antibodies specific for surface or intracellular markers.

In the case of lines derived from dendritic cells the antibodies N418 recognizing the CD11c molecule (Metlay et al., J. Exp. Med. 171, 1753–1771 (1990)) M342 (Agger et al., J. Leukoc. Biol. 52, 34–42 (1992)) and 2A1 (Inaba et al., J. Exp. Med. 175, 1157–1167 (1992)) may be used. The use of those antibodies as well as many other recognizing other specific markers show that CD lines have many of the characteristics reported for Langerhans cells (De Paufilis et al., J. Invest. Dermatol. 93, 60–69 (1989)) and for DC (Inaba K. et al., J. Exp. Med. 176, 1963–1702 (1992)).

The stimulatory activity of DC is partially connected with the presence of the membrane protein B7/BB1 which has been identified on several APC types (Linsley P. S. et al, J. Exp. Med. 173, 721–730 (1991); Linsley P. S. et al., Science 257, 792–795 (1992)) and is considered essential for the induction of virgin T lymphocytes proliferation in MLR assays (Mixed Lymphocyte Reaction) and in inducing an antigen specific proliferative response in lymphocytes expressing the CD4 marker (Larsen C. P. et al, J. Exp. Med. 176, 1215–1220 (1992)). It is possible, for instance, to measure the expression of B7/BB1 by means of flow cytofluorimetry. The result shows that in the DC clones the B7/BB1 gene is constitutively expressed.

The stimulatory activity of DC in a primary MLR (Steinman R. M. et al., J. Exp. Med. 157, 613–617 (1983)) is a typical characteristic of these cells. The CB1 cell line has a stimulating activity in inducing a primary proliferative response in lymphocytes in vitro in an allogenic reaction of MLR type.

A further functional characteristic of DC consists in an the capacity of stimulating in antigen-specific way both T lymphocytes activated by the first contact with the antigen and virgin T lymphocyts (Romani N. et al., J. Exp. Med. 169, 1169–1178 (1989); de Brujin M. L. H. et al., Eur. J. Immunol. 22, 2347–2352 (1992); Croft M., J. Exp. Med. 1765, 1431–1437 (1992)).

The cell lines of the invention may be used to induce in vivo a primary antigen-specific response and without the adjuvant's help. The DC may be administered in vivo after in vitro exposure to the antigen.

They are able to process and present a native antigen such as myoglobin of whale sperm, to a T-cell clone specific for this antigen.

The DCs are also able to induce cell-mediated responses such as contact sensitivity (Sullivan S. et al., Immunol. 137, 2460–2467 (1986)), the graft rejection of allogenic transplants (Lechler R. I. et al., J. Exp. Med. 155, 31 (1982); Larsen C. P. et al., J. Exp. Med. 172, 1483 (1990)), the activation of MHC restricted T-lymphocytes (Inaba K. et al., 172, 631 (1990)) and T-lymphocytes mediated antibodies (Sornasse et al., J. Exp. Med 175, 15–21 (1992)).

The contact sensitivity (CS) is a particular kind of delayed immune response occurring when the organism is immunized at the epicutaneous level and subsequently receives a stimulation with the reactive hapten (Sullivan S. et al., J. Immunol. 137, 2460–2467). It is possible to evidence CS even when Langherans cells or DC are conjugated in vitro with the hapten and then injected into a syngeneic organism (Macatonia S. E., Immunology 59, 509–514 (1986)). The CB1 cells exposed to FITC or DNBS and then injected s.c. in native syngeneic mice are able to induce a primary response of CS type. The response is measured as swelling of the mouse ear into which the cells have been injected; 10000 cells are sufficient to induce a CS response.

This response is antigen specific since untreated CB1 cells cannot generate induction. Therefore CB1 cells are able to induce in vivo the activation of virgin T lymphocytes. The cell lines of the invention have several advantages making them particularly useful.

For example, CB1 cells can be used to stimulate ex vivo antigen specific T lymphocytes. Another example is the possibility to introduce these cells into an organism in order to stimulate T lymphocytes in vivo. The antigen can be administered contemporaneously or separately or, in the case of pathogens, it may be already present in the organism. An additional advantage of CB1 cells is that the antigen can be loaded in vitro before the introduction of the cells in vivo, thus allowing a much more limited amount of antigen or allowing the in vitro processing of the antigen without the need to inject it in vivo as a soluble protein.

A further advantage of these cell lines is that they can be used to induce an immune response different from that obtained by injecting directly the antigen alone or in conjuction with one or more adjuvant; in particular these cell lines can be used to induce T helper lymphocytes subsets such as the TH1 and TH2 subpopulations.

The molecular cloning of the provirus has the advantage to allow modifications by genetic engineering and be used as a retroviral vector.

The cell lines of the invention may be used for the isolation of components or products which cannot be usually obtained because of the limited proportion of APC, particularly DC, within the organs where these cells have been evidenced.

The following examples further illustrate the invention without limiting the scope thereof.

The cells used in the examples are either commercially available or reported in scientific literature. The cells were generally cultivated in RPMI, containing 2 mM β-mercaptoethanol, 10% heat-inactivated fetal calf serum and kept at 37° C. in humidified atmosphere containing 5% $CO_2$.

Recombinant DNA Methods

When available, analytical grade reagents were used. If not otherwise stated, liquid and solid culture media were prepared according to Maniatis T. et al., Molecular Cloning, a Laboratory Manual, Cold Spring Harbor Lab. (1982), hereinafter referred to as "Maniatis".

Immunological Analysis Techniques

Analytical grade reagents were used. If not otherwise stated, the media for cell cultures, the buffer and washing solutions and the other methods used were carried out according to Coligan J. E. et al., "Current Protocols in Immunology" 1992 (J. Wiley and Sons Inc.; Media, Pa.- USA) hereinafter defined as "Coligan".

Example 1

A genomic DNA library from N11 cell line in the pUC18 plasmid was prepared according to known methods (Maniatis T. et al., Molecular Cloning, a Laboratory Manual, Cold Spring Harbor Lab. (1982)). Methods for the library screening and for the probe preparation by nick translation are known and disclosed in Maniatis et al. The ligation product of the genomic DNA fragments generated by digestion with HindIII and EcoRI and inserted into linearized pUC18 plasmid by the same methods used to transform bacterial cells of the HB101 E. coli strain made competent for the incorporation of hexogenous genetic material (Maniatis).

The cells were then plated on solid LB-agar medium containing ampicillin at such a dilution so as to allow to obtain single colonies isolated one from the other.

After growth at 37° C. for 18 h the colonies were transferred onto nitrocellulose further (Schleicher and Schuell Co.). The filters were dried, washed and treated under vacuum at 70° C. (Maniatis). The pre-hybridization, hybridization with a labelled probe derived from a myc-$MH_2$ gene fragment contained in the pMH2Hd plasmid were carried out according to Maniatis.

After suitable washings the filters were dried and exposed to X-ray films which are developed after 12–24 hours. After this screening, the colonies found positive in an identical position on duplicate filters were isolated and plated on LB-agar medium containing ampicillin so as to obtain colonies certainly deriving from a single transformed cell.

These colonies are then subjected to a second selection cycle identical to that previously described. Practically all colonies gave a positive signal in the second screening cycle. One of these was chosen for further studies and named p316.

The insert was completely sequenced according to Sanger using commercially available reagents and the producer's instructions.

Example 2—Preparation of a Line Producing the Retroviral Vector MIB-psi2-N11

The virus VN11 genome cloned into plasmid p316 was co-transfected with the neo gene, derived from transposon TN5 and conferring resistance to the neomycin analogue G418, into the cell line psi. This line is able to form infective viral particles when transformed with an exogenous genetic material containing informations in trans for the inclusion of the RNA produced in the viral particle. The transformed clones were first selected for the growth capacity in the presence of the G418 antibiotic and subsequently for the presence of genomic RNA coded by the VN11 provirus using a probe specific for the v-myc-MH2 gene. The so obtained retroviral vector was named MIB-psi2-N11.

Example 3—Generation of Dendritic Cell Lines

Spleen cell suspensions were prepared from newborn DBA/2 or BALB/C mice (Charles River, Italy) by lysing erythroid cells in ammonium chloride so as to remove erythrocytes according to known methods (Caligan). The cells were then suspended in RPMI-1640 (Sigma) supplemented with 10% FCS (GIBCO), glutamine, penicillin, streptomycin and 0.5 mM β-mercaptoethanol and plated at $10^6$/ml density in 35 mm Petri dishes. Immortalization was carried out with the MIB-psi2-N11 retroviral vector by filtering on 0.22$\mu$ sterile unit (Nalgene) the supernatant surnatant obtained after 24 hr subconfluent culture of the viral producer cell line diluted 1:1 with complete medium containing 10 $\mu$g/ml polybrene (Sigma). After 1 hr incubation at 37° C. in a 5% $CO_2$ incubator, half volume of fresh medium was added and then regularly changed twice a week. During the first week after infection, cells were fed with 10% L929.6C-conditioned media, reduced at 5% in the following two weeks, and then gradually eliminated.

About 20–30 days after infection, multiple foci of dividing cells were observed in the Petri dishes. The cell line was considered established after 20 passages. Once stabilized these lines were plated in 96 well plates by limiting dilution and cloned.

Example 4—Northern Blot Analysis

Northern blot analysis of mRNAs from CB1 cells and a positive control was carried out using a specific myc MH2 probe previously described (Proc. Natl. Acad. Sci. USA, 88, 7546, 1991). The myc MH2 3' probe was derived from a chicken genomic library and it represents the 3' region of the avian myc gene which does not cross-hybridize with the murine myc genes.

Example 5—Immunohistological Analysis of Dendritic Cell Lines

The clones CB1 and D2SC/1 were characterized in more detail by means of antibodies specific for surface of intracellular markers of the dendritic cells such as the N418 anti, CD11c and anti B7 antibodies. These antibodies have been disclosed in the above reported references and were labelled with biotin using known methods (Coligan). Briefly $10^6$ cells were incubated at room temperature for 15' in PBS containing 10% non-immune mouse or rat serum; this solution was then substituted with the primary antibody labelled with biotin in PBS containing 0.1% w/v BSA (Sigma) and the sample was incubated for 30 at 4° C.; the cells were then washed 3 times with PBS containing 0.1% w/v BSA (PBS/BSA) and incubated for 30' at 4° C. with a PBS/BSA solution containing streptavidin/Phycoerythrin (Boehringer) according to the producer's instructions.

The cells were then analyzed by laser pulse flow cytofluorimetry (FACSort, Beckton & Dickinson); the dead cells were eliminated by means of the data analysis pre-treating them with propidium iodide.

| | Comparison of published spleen Dendritic cell surface markers with the CB1 and D2SC/1 cell lines | | | | |
|---|---|---|---|---|---|
| ANTIGEN | Crowley et al. 1989 (Steinman) | Vremec et al. 1992 (Shortman) | Agger et al. 1990 | D2SC/1 | CB1 |
| MHCI | ++ | ++++ | +++ | D +++<br>K n.d.<br>L (AP+++) | D +<br>K n.d.<br>L (AP+++) |
| MHC II | +++ | ++++ | +++ | I-A ++<br>I-E ++ | I-A +<br>I-E + |
| CD8α | −/++* | ±/+++* | −/+* | ± | ± |
| IL2-Rα | ± | − | ± | − | − |
| CD28 | n.d. | n.d. | n.d. | ++ | ++ |
| B7 | n.d. | n.d. | n.d. | + | ++ |
| CD2 | n.d. | + | n.d. | + | + |
| CD11a (LFA-1) | n.d. | n.d. | + | ++ | ++ |
| CD54 (ICAM-1) | n.d. | n.d. | n.d. | +++ | +++ |
| C11b (Mac-1) | + | + | + | n.d. | n.d. |
| CD11c (N418) | n.d. | n.d. | ++ | ++ | ++ |
| α4 Integrin (R1-2) | n.d. | n.d. | n.d. | +++ | ++ |
| CD18 | n.d. | n.d. | +++ | +++ | +++ |
| CD44 (Pgp-1) | ++ | ++++ | n.d. | ++++ | ++++ |
| HSA (J11D) | −/++* | +++ | −/+* | +/+++* | +/+++* |
| B220 | − | − | − | − | − |
| F4/80 | ± | + | − | ++ | + |
| CDw32 (FcγII) | − | + | − | ++ | + |
| FcεRI + II | n.d. | n.d. | n.d. | − | − |

− negative
± <10%
+ 10–50%
++ 50–90%
+++ >90%
++++ 100%, mean >50x over background
n.d. not detected
AP H-2 L restricted antigenpresentation
*two populations
Agger R., Crowley M. T. and Witmer-Pack M. D. 1990, Intern. Rev. Immunol. 6:89–101,
Crowley M., Inaba K., Witmer-Pack M. and Steinman R. M. 1989, Cellular Immunology 118:108–125,
Vremec D., Zorbas M., Scollay R., Saunders D. J., Ardavin C. F., Wu L. and Shortman K. 1992, J. Exp. Med. 176:47–58.

Example 6—Immunohistochemical Analysis

For the analysis of intracellular markers, the CB1 cells were grown as above on sterile glasses and then fixed in acetone for 2' at room temperature. The cells were then incubated with the first antibody for 1 hour at room temperature in PBS containing 1% of non-immune mouse serum, washed three times with PBS/BSA and then incubated with peroxidase labelled mouse antibodies against rat Igs (2A1 antibody) or against hamster Igs (M342 antibody). The cells were then incubated in the presence of diamino benzidine so as to evaluate the positivity thereof.

Example 7—Analysis of the in Vitro Stimulatory Activity of CB1 Cells

The Mixed Lymphocyte Reaction (MLR) assay was carried out using a spleen cell suspension obtained as described above from allogeneic C57BL/6 mice. CB1 dendritic cells or the macrophage cell line MT2/1 (P. Ricciardi-Castagnoli et al., 1992. Res. Immunol. 143, 101–106) were used as stimulating cells pre-treating them with 25 μg/ml of Mitomycin C for 20' at 37° C. in polystyrene test tubes. After washing, the stimulating cells are washed with complete medium and plated on 96 will plates at decreasing doses together with 30.000 cells/ml of T cells deriving from C57BL/6 mice. The cells were co-cultured in the presence of complete medium containing 2 μCi/ml of 3H-TdR. T cells were obtained from the splenic cell suspension by purification on nylon membrane. The cells were incubated for 72 hours in the above reported conditions, filtered on filter-glass filter and the incorporated radioactivity was measured by liquid scintillation counter (Betaplate, LKB-Wallac).

The presentation assay of the antigen was carried out adding decreasing doses, starting from 0.5 μM, of whale sperm myoglobin (SpWMb) at 10000 cells APC (CB1) preactivated with 100 U/ml of IFN/γ or 200 μg/ml of mrGM/CSF. The pre-activated APC were then co-cultivated with 10000 cells of the murine T—T hybridoma 13.26.8 (obtained from Dr. A. Livingstone, Basel Institut for Immunology, Basel, CH) in flat-bottom, 96-wells plates. After 24 hours of growth in Iscove (Sigma) medium containing antibiotics, glutamine and Beta-mercaptoethanol as above reported and 5% fetal bovine serum, 100 μl of supernatant surnatant from each well were transferred to 96-will plates containing cells of the IL-2-dependent HT.2 line and assayed for the IL-2 content according to the described method (Coligan) using a calorimetric assay based on MTT (Sigma).

Example 8—Analysis of the Capacity of CB1 Cells of Inducing T-Dependent Responses in Vivo CB1 cells were derivatized with 200 μg/ml of FITC (Sigma) or with 1 mg/ml DNBS (2,4-dinitro benzene sulfonic acid, Eastman Kodak) for 30' at 37° C. according to the method disclosed by Macatonia S. E. et al., Immunology 59, 509–514, 10.000 cells were injected in a volume of 250 μl of HBSS (Sigma) subcutaneously in the back of syngeneic mice. After 5 days, mice injected with derivatized cells or with non-derivatized cells as a control, were treated with 25 μg of FITC or with 15 μg of DNFB (2,4-dinitro-1-fluorobenzene, Sigma) on both sides of each ear. The ear thickness was measured with a micrometer immediately before treatment and after 24, 48 and 72 hours.

Example 9—Possibility of Obtaining MHC⁻ Variants of Dendriditic Cells Deletion Mutants in the MHC Genes Cultured cells were mutagenized by gamma rays with doses ranging from 300 to 1000 rad from a cesium source and negatively selected with anti-MHC molecules type I an II antibodies and subsequent treatment with Complement.

According to the method disclosed by Moretta et al. (Proc. Natl. Acad. Sci. USA, 84, 1654–1658, 1987) it is possible to select, by cytofluorimetry, negative (or double-negative) variants for the expression of MHC genes obtained after irradiation.

By this method, it was possible to obtain MHC⁻ (negative) dendritic cell lines which can be subsequently transfected with the desired class I or class II (MHC) genes. For instance, a plasmid containing the cDNA of the neo gene has been transfected into dendritic cells by means of lypofectin: to this purpose, $1\times10^6$ cells were plated in 2 ml of culture medium to which a solution containing 5 μg of DNA in 50 μl of culture medium have been added. After 16 hours, further 2 ml of culture medium were added and the incubation continued for further 48 hours before starting the transfectants selection.

Utility

The present invention provides means for activating T-lymphocytes in an antigen-specific way both in vivo and in vitro.

For instance, it is possible to remove T cells from the organism, stimulating those specific for a given antigen and re-introducing them in the same organism so as to provoke an immune response to that antigen. On the other hand, the cell lines of the invention may be sensitized with a given antigen and then re-introduced into an MHC compatible organism. In particular, this invention is useful in those cases where the antigen purification is difficult or expensive, in the cases where the organism against which an immune response should be elicited is dangerous to handle or when vaccination with the same organism gives side-effects and moreover in those cases where it is usually difficult to elicit an effective and long-lasting immune response.

I claim:

1. Isolated immortalized mammalian dendritic cells which have been transduced with a VN11 retroviral vector containing a v-myc oncogene, wherein expression of the oncogene results in the immortalization of the dendritic cells, wherein said immortalized mammalian dendritic cells retain the function of processing and presenting antigen.

2. The isolated immortalized mammalian dendritic cells according to claim 1, wherein the retroviral vector is obtained by co-transfection of an MH2 retrovirus and an AKR retrovirus, wherein at least one of the retroviruses contains the v-myc oncogene.

3. The isolated immortalized mammalian dendritic cells according to claim 2, wherein the v-myc oncogene is fused to an envAKR gene.

4. The isolated immortalized mammalian dendritic cells according to claim 3, wherein the oncogenic retroviral vector is obtained from murine macrophage cell line N11 deposited at European Collection of Animal cell Cultures under accession number 93051207.

5. The isolated immortalized mammalian dendritic cells according to claim 1, wherein the oncogenic retroviral vector is isolated from "packaging" cell lines.

6. The isolated immortalized mammalian dendritic cells according to claim 5, wherein the oncogenic retroviral vector is isolated from psi2 cells transfected by the VN11 virus of an N11 cell line.

7. The isolated immortalized mammalian dendritic cells according to claim 6, wherein the oncogenic retroviral vector is the MIB-psi2-N11 vector.

8. The isolated immortalized mammalian dendritic cells according to claim 1, wherein said immortalized dendritic cells were isolated from a source of dendritic cells from the group consisting of dendritic cells from bone marrow and peripheral blood, Langerhans cells from the epidermis, follicular and interstitial dendritic cells from germinal centers and interdigitating dendritic cells from the lymphoid organs, prior to immortalization.

9. A process for immortalizing mammalian dendritic cells comprising transfecting primary cultures of mammalian dendritic cells with a VN11 retroviral vector containing a v-myc oncogene, wherein the expression of said oncogene results in the immortalization of said dendritic cells, and wherein the resulting immortalized mammalian dendritic cells retain the function of processing and presenting antigen.

10. The process according to claim 9, in which the VN11 retroviral vector is obtained from murine macrophage N11 cell line deposited at the European Collection of Animal Cell Cultures under accession number 93051207.

11. The process according to claim 10, wherein the transfection is obtained by co-cultivation of dendritic cells with packaging cell lines transfected by a VN11 virus produced by an N11 cell line.

12. The process according to claim 11, wherein the packaging cell line is the psi2 line.

* * * * *